(12) United States Patent
Bonda et al.

(10) Patent No.: US 8,425,888 B1
(45) Date of Patent: Apr. 23, 2013

(54) SILICONE BENZYL ESTERS

(75) Inventors: Craig Bonda, Winfield, IL (US); Jean Zhang, Hickory Hills, IL (US); Kevin O'Lenick, Smyrna, GA (US)

(73) Assignee: The HallStar Company, Chicago, IL (US)

( * ) Notice: Subject to any disclaimer, the term of this patent is extended or adjusted under 35 U.S.C. 154(b) by 0 days.

(21) Appl. No.: 13/385,148

(22) Filed: Feb. 6, 2012

(51) Int. Cl.
*A61Q 5/12* (2006.01)

(52) U.S. Cl.
USPC .......................................................... 424/70.12

(58) Field of Classification Search ........................ None
See application file for complete search history.

(56) References Cited

U.S. PATENT DOCUMENTS 6,552,212 B2    4/2003   Walele et al.

*Primary Examiner* — Paul Dickinson

(57) ABSTRACT

The present invention relates to a series of dimethicone esters that contain benzyl groups. These esters have a dry feel and are well suited to a variety of uses especially cosmetic uses where they fond use in sunscreen compositions, pigment dispersions, and creams and lotions.

11 Claims, No Drawings

SILICONE BENZYL ESTERS

GOVERNMENT SPONSORSHIP

None

FIELD OF THE INVENTION

The present invention relates to a series of dimethicone esters that contain benzyl groups linked through an eleven carbon ester group to silicone. These esters have a dry feel and are well suited to a variety of uses especially cosmetic uses where they fond use in sunscreen compositions, pigment dispersions, and creams and lotions.

BACKGROUND

Benzoate esters that do not contain silicone are known in the art.

U.S. Pat. No. 4,278,655 to Elmi describes the use of benzoic acid esters of a mixture of linear primary alcohols in the C9 to C15 carbon chain length range in anti-perspirant compositions.

U.S. Pat. No. 4,275,222 to Scala, Jr., describes the benzoic acid esters of a mixture of C12, C13, C14 and C15 linear primary alcohols. The compositions described therein are said to have anti-foaming properties, i.e. they prevent foam from forming initially, and are used in hand cleaners, dispersible bath oils, and floating bath oils.

U.S. Pat. No. 4,293,544 to Elmi describes the use of benzoic acid esters of a mixture of C12, C13, C14 and C15 linear primary alcohols in toiletries, cosmetics, topical pharmaceuticals and the like.

U.S. Pat. No. 4,322,545 to Scala, Jr. describes benzoic acid esters wherein the alcohol is from C12 to C15 primary alcohols. The compositions described therein are said to lack greasiness, oiliness, have a low cloud point and pour point, bland odor, ability to form gels with suspending agents and low toxicity. U.S. Pat. No. 4,323,693 to Scala, Jr. describes a substantially pure benzoic acid ester of isostearyl (C18) alcohol for use as a carrier or vehicle, emollient or solublizer for cosmetic and toiletry formulations. U.S. Pat. No. 4,323,694 to Scala, Jr. describes benzoic acid esters of alcohols which are branched primary alcohols up to C18 and branched or linear alcohols up to C19.

U.S. Pat. No. 6,552,121 issued Apr. 22, 2003 to Walele teaches Compositions of matter comprising benzoate esters of hydroxyl terminated polyether polysiloxane copolyols, in particular dimethicone copolyol benzoates, and process for preparing same. The benzoate esters are useful for personal care cleansing products, such as bar and liquid soaps, skin and hair care products and textiles and fibers. The compounds are prepared by reacting benzoic acid with hydroxyl terminated polyether polysiloxane copolyols.

None of the patents have the critical undecylenic linkage described in the present invention. This group provides a C11 alkyl group improving oil solubility, is free of ethylene oxide and provides raw materials suitable to run a hydrosilylation reaction lacking in the Walele patent.

Unlike the compounds referenced above, we have surprisingly learned that when benzyl undecylenate is reacted with a specific silanic hydrogen containing polymer to make a compound with an aromatic group containing benzyl ester on the end of an alkyl oil soluble linking group which is in turn linked to a silicone group. The ability to manipulate the ratio of the silicone, fatty and aromatic group results in a wide range of multi functional molecules that have solubility in a variety of solvents ranging from fatty, to silicone providing unique properties.

THE INVENTION

Objective of the Invention

The objective of the present invention is to provide a series of silicone polymers that contain (a) a silicone group bonded directly to (b) an alkyl group having ten carbons (C) onto which is esterfied a benzyl group.

The compounds so configured have unique solubility properties, skin feel and aesthetics heretofore unattainable using benzyl esters of non-silicone compounds.

SUMMARY OF THE INVENTION

The present invention is directed to the hydrosilylation product of specific silanic hydrogen compounds and benzyl undecylenate The resulting polymer allows for the formulation of skin care, pigmented care and suncare products that have unique properties.

All percentages given herein are percentages by weight, all temperatures are degrees C. and all referenced patents are incorporated herein by reference as allowed.

DETAILED DESCRIPTION OF THE INVENTION

The intermediate useful in the preparation of the compounds of the present invention conform to the following structure:

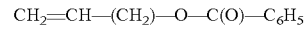

wherein $C_6H_5$ is

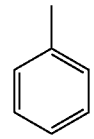

One aspect of the present invention is compounds conforming to the following structure:

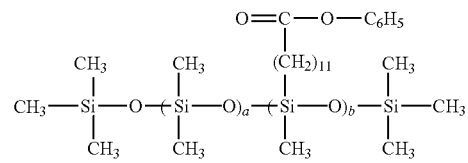

wherein:

a is an integer ranging from 0 to 200;

b is an integer ranging from 2 to 20;

$C_6H_5$ is

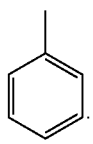

Another aspect of the present invention is a process for the conditioning of hair or skin which comprises contacting the hair or skin with an effective conditioning concentration of a compound conforming to the following structure:

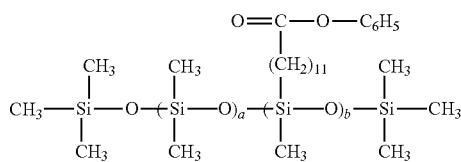

wherein:
a is an integer ranging from 0 to 200;
b is an integer ranging from 2 to 20;
$C_6H_5$ is

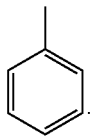

In a preferred embodiment the conditioning concentration ranges form 0.1 to 20% by weight.

Preferred Embodiments

In a preferred embodiment b is an integer ranging from 2 to 10.

In a preferred embodiment b is an integer ranging from 2 to 5.

In a preferred embodiment b is an integer ranging from 6 to 20.

In a preferred embodiment a is an integer ranging from 1 to 200;

In a preferred embodiment a is an integer ranging from 2 to 100.

In a more preferred embodiment a is 0.

EXAMPLES

Preparation of benzyl undecylenate

Benzyl undecylenate is made using the following procedure:
To 580 grams of undecenyl methyl ester (CAS 5760-50-9), is added 420 grams of benzyl alcohol (CAS 100516). Next add, 0.1% by weight of stannous oxalate. This mixture was heated to 175° C. over a half hour period and held for 8 hours, until the acid value is below 5 mg KOH/gm.

Upon cooling to 90 C., 2.0 gm. hydrogen peroxide was added to bleach the slight darkening in the reaction mixture. The reaction mixture was then cooled to 30 C. Upon treatment for 10 minutes with 10.0 gm. CELATOM FW-60, the product is filtered at 50-60 C, resulting in a clear yellow liquid.

150 gms. of the product above is treated with 3.4 gms of sodium carbonate, 3.4 gm. of sodium sulfate and 102.2 gm. of water at 80-85 C. The wet top layer of the mixture (162.5 gms.) was then treated with two washes; each consisting of 3.5 gm of sodium sulfate and 100 gms. of water. The product layer upon separation was 160 gms. which was dried at 90-100 C. under vacuum of 27" Hg.

Upon cooling to 60-65 C. and the addition of 0.25 gms. of CELATOM FW-60, the ester was filtered using Whatman #2 paper. A clear refined liquid ester was obtained.

The resulting product is $CH_2=CH-(CH_2)_{11}-C(O)-O-C_6H_5$.

Silicone Intermediates

Silicone Intermediates useful in the synthesis of the compounds of the present invention conform to the following structure:

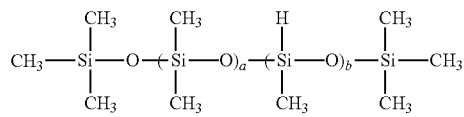

wherein:
a is an integer ranging from 0 to 200;
b is an integer ranging from 2 to 20.

They are commercially available form Siltech LLC and are sold under the Silmer® H trademark. Silmer® is a registered trademark of Siltech.

| Example | "a" | "b" |
|---|---|---|
| 1 | 1 | 0 |
| 2 | 1 | 1 |
| 3 | 2 | 5 |
| 4 | 5 | 10 |
| 5 | 10 | 100 |
| 6 | 20 | 200 |
| 7 | 20 | 0 |
| 8 | 10 | 20 |
| 9 | 10 | 100 |
| 10 | 20 | 200 |

Compounds of the Present Invention

To 330 grams of the benzyl undecylenate is added the specified number of grams of the specified silanic hydrogen compound (Example 1-10). The reaction mass is mixed well until homogeneous. To that mixture is added 0.1% Karstedt catalyst, which is commercially available from Geleste. The agitation is stopped and the reaction begins. The reaction mass is reacted for 4 hours. The product may be sold as prepared without additional purification.

| Example | Example | Grams |
|---|---|---|
| 11 | 1 | 224 |
| 12 | 2 | 298 |
| 13 | 3 | 327 |
| 14 | 4 | 241 |
| 15 | 5 | 816 |

| Example | Example | Grams |
|---|---|---|
| 16 | 6 | 808 |
| 17 | 7 | 768 |
| 18 | 8 | 224 |
| 19 | 9 | 816 |
| 20 | 10 | 808 |

Applications

The compounds of the present invention offer the possibility of altering the ration of "a" to "b". This means that the percentage oil soluble to silicone soluble can be precisely tailored to specific applications. The ability to alter the solubility of the ester in silicone solvents and organic solvents makes the compounds of the present invention well suited to skin care products, pigmented products and sun care products.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:

1. A silicone conforming to the following structure:

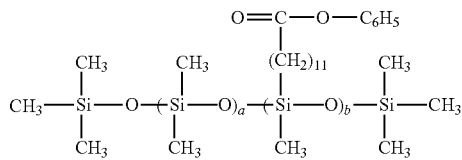

wherein:
a is an integer ranging from 0 to 200:
b is an integer ranging from 2 to 20;
$C_6H_5$ is

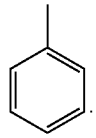

2. A silicone of claim 1 wherein a is an integer ranging from 1 to 200; and b is an integer ranging from 2 to 20.

3. A silicone of claim 1 wherein a is an integer ranging from 2 to 100 and b is an integer ranging from 2 to 20.

4. A silicone of claim 2 wherein b is an integer ranging from 2 to 10.

5. A silicone of claim 2 wherein b is an integer ranging from 2 to 5.

6. A silicone of claim 2 wherein b is an integer ranging from 6 to 20.

7. A silicone of claim 3 wherein b is an integer ranging from 2 to 10.

8. A silicone of claim 3 wherein b is an integer ranging from 2 to 5.

9. A silicone of claim 3 wherein b is an integer ranging from 6 to 20.

10. A process for conditioning hair and skin which comprises contacting the hair or skin with an effective conditioning concentration of a silicone conforming to the following structure:

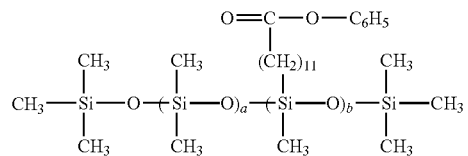

wherein:
a is an integer ranging from 0 to 200;
b is an integer ranging from 2 to 20;
$C6H_5$ is

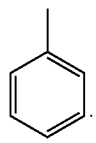

11. A process of claim 10 wherein said conditioning concentration ranges from 0.1 to 20% by weight.

* * * * *